(12) United States Patent
Yuan (10) Patent No.: US 7,680,249 B2
(45) Date of Patent: Mar. 16, 2010

(54) FILTER UNIT, X-RAY TUBE UNIT, AND X-RAY IMAGING SYSTEM

(75) Inventor: Ping Yuan, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 35 days.

(21) Appl. No.: 12/118,398

(22) Filed: May 9, 2008

(65) Prior Publication Data

US 2008/0279337 A1 Nov. 13, 2008

(30) Foreign Application Priority Data

May 11, 2007 (CN) .................. 2007 1 0102914

(51) Int. Cl.
*G21K 3/00* (2006.01)
(52) U.S. Cl. .................. 378/158; 378/156; 378/157
(58) Field of Classification Search .................. 378/5, 378/16, 98.9, 98.11, 156, 157, 158, 159
See application file for complete search history.

(56) References Cited

U.S. PATENT DOCUMENTS

| | | | |
|---|---|---|---|
| 3,631,249 A | 12/1971 | Friede et al. | |
| 3,917,954 A | 11/1975 | Boge | |
| 3,943,366 A | 3/1976 | Platz et al. | |
| 4,300,055 A | 11/1981 | Taumann | |
| 4,347,440 A | 8/1982 | Haas | |
| 4,528,453 A | 7/1985 | Heller | |
| 4,597,096 A | 6/1986 | Larsson | |
| 5,107,529 A * | 4/1992 | Boone | 378/157 |
| 5,148,465 A | 9/1992 | Mulder et al. | |
| 5,396,889 A * | 3/1995 | Ueda et al. | 600/407 |
| 5,512,754 A | 4/1996 | Enos | |
| 5,519,223 A | 5/1996 | Hug et al. | |
| 5,680,434 A * | 10/1997 | Thelosen et al. | 378/150 |
| 5,689,544 A * | 11/1997 | Van Den Besselaar | 378/150 |
| 5,991,362 A * | 11/1999 | Jones | 378/152 |
| 6,036,632 A * | 3/2000 | Whitmore et al. | 600/7 |
| 6,148,062 A * | 11/2000 | Romeas | 378/156 |
| 6,226,352 B1 * | 5/2001 | Salb | 378/98.9 |
| 6,597,758 B1 * | 7/2003 | Rosner | 378/53 |
| 6,614,878 B2 * | 9/2003 | Bogatu et al. | 378/158 |
| 6,624,431 B1 | 9/2003 | Foster et al. | |
| 6,633,627 B2 * | 10/2003 | Horiuchi | 378/156 |
| 7,260,183 B2 | 8/2007 | Yuan et al. | |
| 7,263,171 B2 * | 8/2007 | Zhang | 378/160 |
| 2004/0264647 A1 | 12/2004 | Graf et al. | |
| 2006/0182226 A1 | 8/2006 | Yuan et al. | |

FOREIGN PATENT DOCUMENTS

JP 2006-226985 8/2006

* cited by examiner

*Primary Examiner*—Allen C. Ho
(74) *Attorney, Agent, or Firm*—Armstrong Teasdale LLP (57) ABSTRACT

A small-sized filter unit of a simple structure, as well as an X-ray tube unit and an X-ray imaging system both having the filter unit, are implemented. A filter unit in a first aspect of the present invention comprises a filter plate, the filter plate having a first filter, a second filter disposed in a first direction with respect to the first filter and a third filter disposed in a second direction having a predetermined angle from the first direction with respect to the first filter, a guide plate having a guide frame for movement of the filter plate in the first and second directions, and a drive device for moving the filter plate.

20 Claims, 6 Drawing Sheets

FILTER UNIT, X-RAY TUBE UNIT, AND X-RAY IMAGING SYSTEM

CROSS REFERENCE TO RELATED APPLICATIONS

This application claims the benefit of Chinese Patent Application No. 200710102914.9 filed May 11, 2007, which is hereby incorporated by reference in its entirety.

BACKGROUND OF THE INVENTION

The subject matter disclosed herein relates to a filter unit for adjusting the energy spectrum of X-ray, as well as an X-ray tube unit and an X-ray imaging system both having the filter unit. Particularly, the embodiments described herein are concerned with a filter unit of low cost permitting replacement of plural filters, as well as an X-ray tube unit and an X-ray imaging system.

In an X-ray imaging system, X-ray is radiated to a subject after adjusting its energy spectrum with a filter. The filter is installed within a collimator box attached to an X-ray tube. In the invention of Japanese Unexamined Patent Publication No. 2006-226985, for obtaining a desired spectrum, the filter can be used by switching from one to another among plural filter plates secured to a rotary disc.

For radiating X-ray to a standing subject or to a subject who is lying down, it is necessary for an X-ray tube unit to direct its angle in an arbitrary direction. To meet this requirement it is necessary to reduce the size of the X-ray tube unit. An X-ray irradiation unit disclosed in the above-referenced patent publication permits adjustment in multiple stages, but the size of an X-ray tube unit used is large. Besides, if the X-ray tube unit is provided with plural drive devices such as motors, it becomes complicated in structure and gets out of order more frequently, with an increase of the manufacturing cost.

Accordingly, it is desirable to provide a filter unit simple in structure and small in size, as well as an X-ray tube unit and an X-ray imaging system both having the filter unit.

SUMMARY OF THE INVENTION

For solving the above-mentioned problems, a first aspect provides a filter unit comprising a filter plate, the filter plate having a first filter, a second filter disposed in a first direction with respect to the first filter and a third filter disposed in a second direction having a predetermined angle from the first direction with respect to the first filter, a guide plate having a guide frame for movement of the filter plate in the first and second directions, and a drive device for moving the filter plate.

According to this configuration, the filter plate having at least three filters can move in both first and second directions along the guide frame. Therefore, the filter unit of simple structure is provided.

In a filter unit according to a second aspect, the drive unit comprises a single motor and a rotary disc adapted to rotate by the drive motor.

According to this configuration, the filter plate can be moved in both first and second directions by a single drive motor. Since the filter plate can be moved in plural directions by a single drive motor, the filter unit is simple in structure and small-sized.

In a filter unit according to a third aspect, the rotary disc and the filter plate are connected with each other through a link member.

According to this configuration, since the rotary disc is connected to the filter plate through a link member, a rotational force of the rotary disc is applied to the filter plate.

In a filter unit according to a fourth aspect, a bushing is attached to the link member and is adapted to move along the guide frame.

According to this configuration, the bushing of the link member moves in the first and second directions along the guide frame. Consequently, a rotational force of the rotary disc is applied to the filter plate as a drive force acting in both first and second directions.

In a filter unit according to a fifth aspect, the guide plate is centrally provided with a first aperture, the rotary disc is centrally provided with a second aperture, and the guide plate and the rotary disc are superimposed one on the other.

According to this configuration, the filter plate rotates, centered at the first and second apertures. Besides, since the guide plate and the rotary disc are superimposed one on the other, a small space suffices and it is possible to attain the reduction in size of the filter unit.

In a filter unit according to a sixth aspect, the filter plate has a square outline and the first direction and the second direction are orthogonal to each other.

As can be seen from FIG. 5, if the filter plate has four filters, a square shape thereof is efficient and the filter unit can be constituted while saving space.

A seventh aspect of the present invention provides an X-ray tube unit having an X-ray tube, a collimator and a filter unit, the filter unit comprising a filter plate, the filter plate having a first filter, a second filter disposed in a first direction with respect to the first filter and a third filter disposed in a second direction having a predetermined angle from the first direction with respect to the first filter, a guide plate having a guide frame for movement of the filter plate in the first and second directions, and a drive device for moving the filter plate.

The filter plate has a first aperture formed centrally of the guide plate and a second aperture formed centrally of a rotary disc, the first aperture and the second aperture being in alignment with an axis joining an X-ray tube and an aperture of a collimator.

In an X-ray tube unit according to an eighth aspect, the filter plate has a first aperture formed centrally of the guide plate and a second aperture formed centrally of a rotary disc, the first aperture and the second aperture being in alignment with an axis joining an X-ray tube and an aperture of a collimator.

Further, such an X-ray tube unit is employable in an X-ray imaging system.

According to such a configuration it is possible to provide an X-ray tube unit simple in structure and small-sized, and an X-ray imaging system using the X-ray tube unit can be reduced in cost. Besides, since the first and second apertures being in alignment with an axis joining the X-ray tube and the collimator aperture, an X-ray beam emitted from the X-ray tube is not obstructed halfway.

According to the embodiments described herein, a filter unit having at least three filters can be provided in a simple structure and reduced size. Therefore, it is possible to implement a small-sized X-ray tube unit and an X-ray imaging system having such an X-ray tube unit.

DETAILED DESCRIPTION OF THE INVENTION

The best mode for carrying out the present invention will be described in detail hereinunder with reference to the drawings. The present invention is not limited to the best mode for carrying out the invention.

Figure 1:
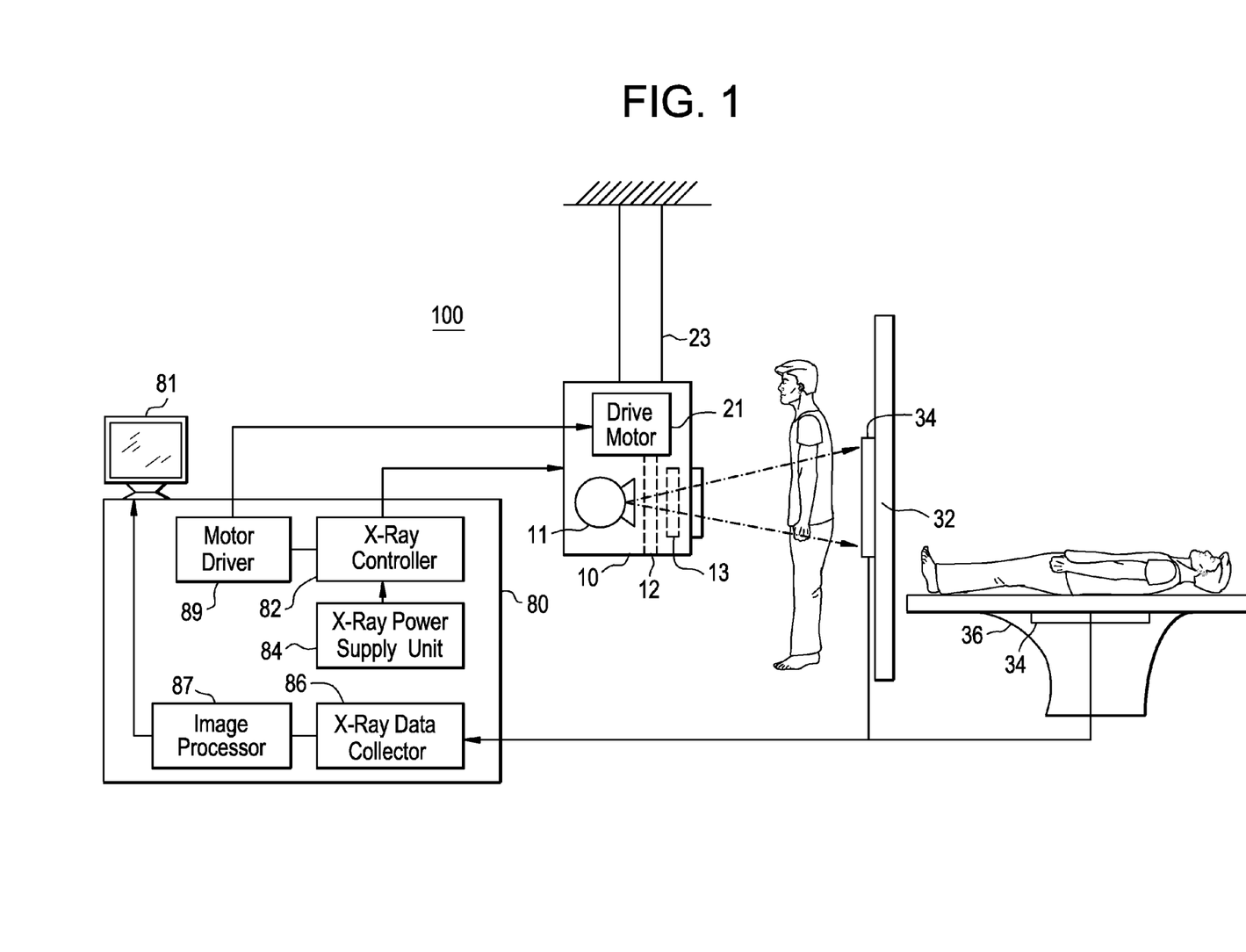
FIG. 1 is a block diagram showing the configuration of an X-ray imaging system 100 for obtaining an X-ray radioscopic image of a subject.

Entire Configuration of X-ray Imaging System. FIG. 1 is a block diagram showing the configuration of an X-ray imaging system (CR: Computed Radiography) 100 for obtaining an X-ray transmitted image of a subject.

System 100 includes an X-ray tube 10 for emitting X-ray, a stand 32 for radiographing a subject in a stand-up state, a table 36 on which the subject is to lie down, and an operator console 80. Flat panel detectors 34 for detecting X-ray after passing through the subject are attached to the stand 32 and the table 36 respectively. The operator console 80 has an X-ray data collector 86 for collecting image data transferred from the flat panel detectors 34. The image data collected and stored by the X-ray data collector 86 are subjected to image processing in an image processor 87 and an X-ray radioscopic image resulting from the image processing is displayed on a display 81.

The X-ray tube unit 10 is suspended from the ceiling in a diagnostic room through a support post 23 which is extended and contracted with a motor (not shown). The X-ray tube unit 10 and the support post 23 are connected with each other by a ball joint structure and the X-ray tube unit 10 is rotatable in any direction. Therefore, X-ray can be radiated in any direction in accordance with a portion to be radiographed of the subject. The X-ray tube unit 10 may be mounted to a movable stand disposed on a floor.

An X-ray power supply unit 84 is provided within the operator console 80 to supply electric power to the X-ray tube unit via an X-ray controller 82. The X-ray tube unit 10 houses therein an X-ray tube 11, a filter unit 12 and a collimator 13. The X-ray tube 11 emits X-ray at voltage and current controlled by the X-ray controller 82. The X-ray emitted from the X-ray tube 11 is adjusted its energy spectrum by the filter unit 12. The collimator 13 has an aperture whose area is changeable and X-ray having been adjusted to an appropriate irradiation area is radiated to a subject through the aperture. The filter unit 12 has plural filters so that the energy spectrum can be changed.

In the X-ray tube unit 10 there is provided a drive motor 21 so that the plural filters in the filter unit 12 can be switched from one to another. The drive motor 21 is driven through a motor driver 89 under control by the X-ray controller 82.

Figure 2A:
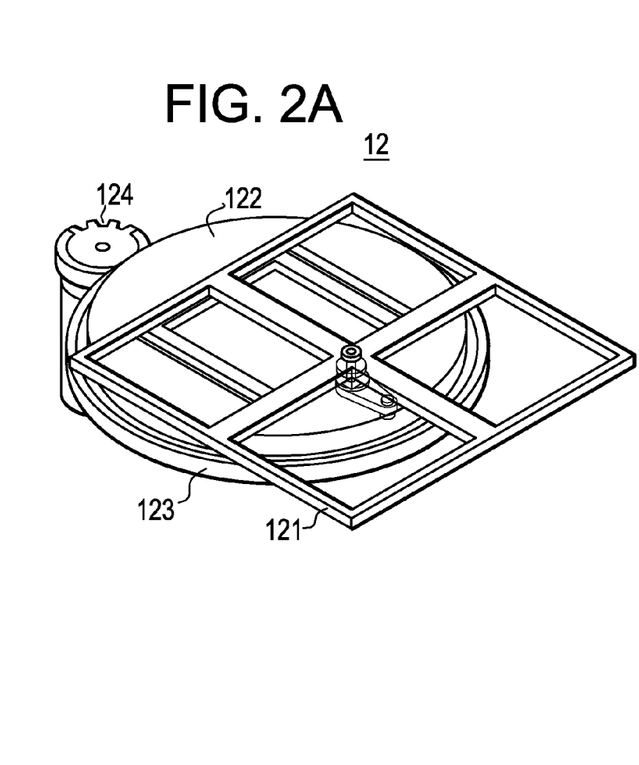
FIG. 2(a) is a perspective view showing a filter unit 12 that may be used with the X-ray imaging system shown in FIG. 1
Figure 2B:
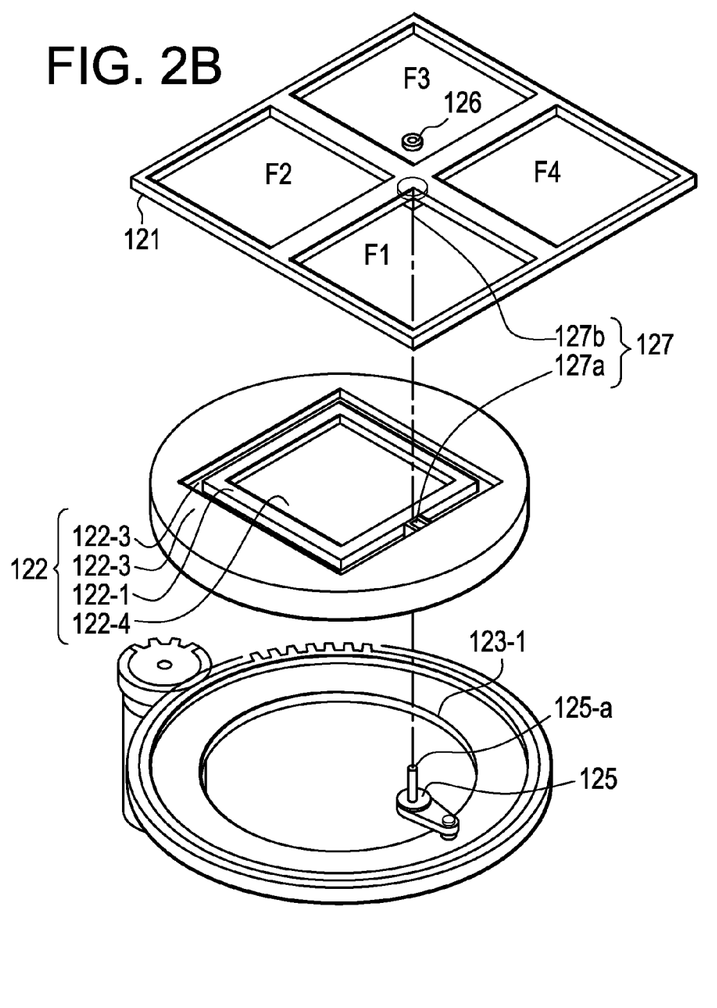
FIG. 2(b) is an exploded view thereof.
Figure 3:
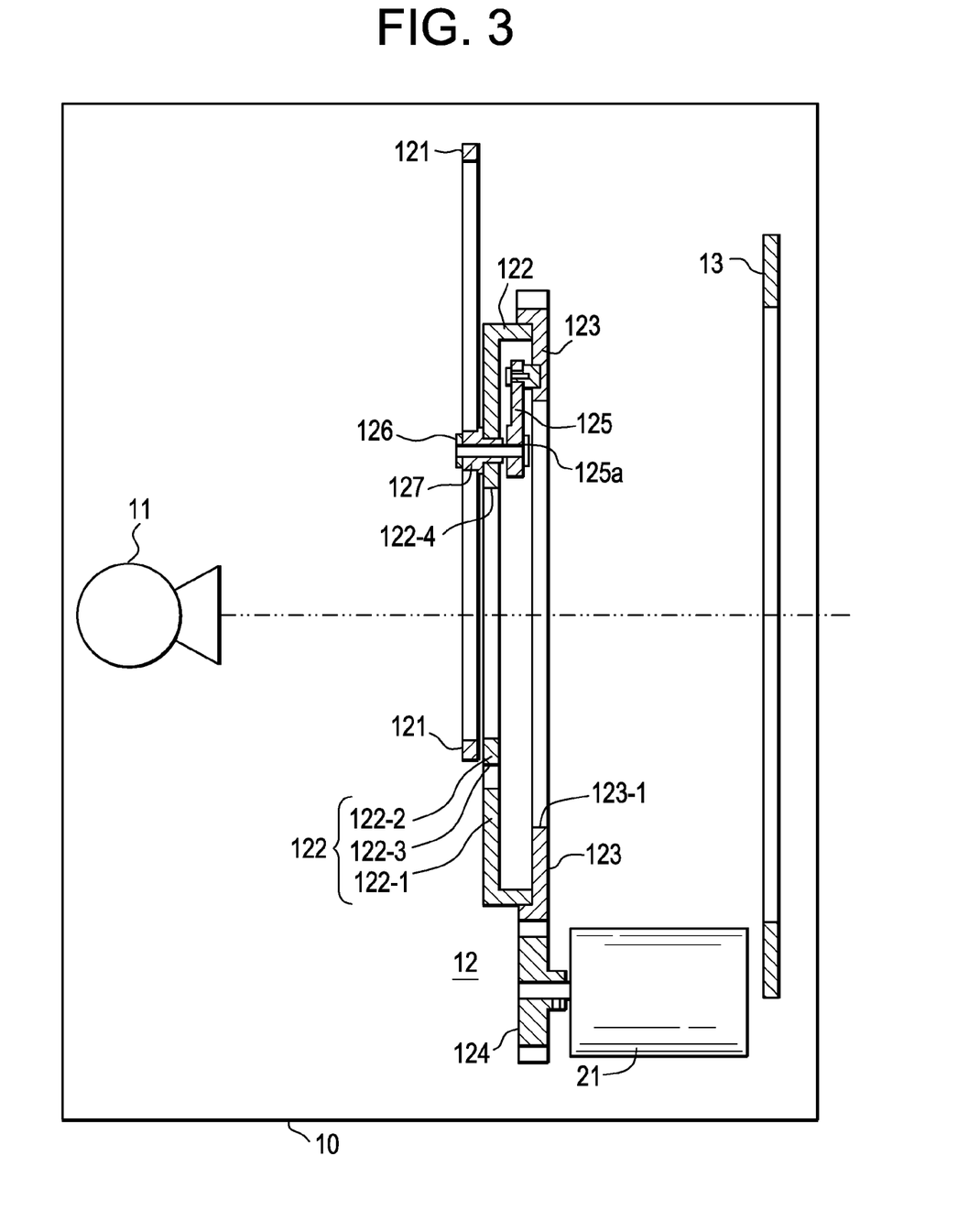
FIG. 3 is a sectional view of the filter unit 12.

Configuration of Filter Unit 12. FIG. 2(a) is a perspective view showing the filter unit 12 according to an embodiment of the present invention and FIG. 2(b) is an exploded view thereof FIG. 3 illustrates the X-ray tube 10, including sectional views of the X-ray tube 11, filter unit 12 and collimator 13.

The filter unit 12 includes a filter plate 121 having four filters, a guide plate 122 for guiding a moving route of the filter plate 121, and a drive plate 123 for moving the filter plate 121 in a predetermined direction.

The filter plate 121 is provided with, for example, a beam attenuating filter F1 of approximately 0.0 millimeters (mm), a beam attenuating filter F2 of approximately 0.1 mm, a beam attenuating filter F3 of approximately 0.2 mm and a beam attenuating filter F4 of approximately 0.3 mm. By the beam attenuating filter F1 of approximately 0.0 mm is meant a filter-free state with only the frame of the filter plate 121 being present. With respect to the beam attenuating filter F1, the beam attenuating filter F2 is disposed in a first direction of the beam attenuating filter F1 and the beam attenuating filter F4 is disposed in a second direction orthogonal to the first direction. The beam attenuating filter F3 is disposed in the second direction with respect to the beam attenuating filter F2. The filters are not limited to beam attenuating filters, but may be any other filters insofar as they change the characteristics of X-ray. One of the filters may be a light shielding filter as a substitute for a light shielding shutter and a metallic sheet having a percentage light shielding of 100% may also be used as one filter.

The filter plate 121 is centrally formed with a hole for passing therethrough of a pin 125-a of a link bar 125 which will be described later. The filters F1 to F4 are square in shape and the size of each filter is between approximately 10.0 square centimeters ($cm^2$) and approximately 15.0 $cm^2$. The filters F1 to F4 may be circular. The filter plate 121 is square in shape and its size is between approximately 20.0 $cm^2$ and approximately 35.0 $cm^2$. The material of the filter plate 121 is, for example, light-weight aluminum.

The filter plate 121 is provided with, for example, a beam attenuating filter F1 of approximately 0.0 millimeters (mm), a beam attenuating filter F2 of approximately 0.1 mm, a beam attenuating filter F3 of approximately 0.2 mm and a beam attenuating filter F4 of approximately 0.3 mm. By the beam attenuating filter F1 of approximately 0.0 mm is meant a filter-free state with only the frame of the filter plate 121 being present.

The filters are not limited to beam attenuating filters, but may be any other filters insofar as they change the characteristics of X-ray.

For guiding a moving route of the filter plate 121, the guide plate 122 is formed with a guide groove 122-3 between an outer guide plate 122-1 and an inner guide plate 122-2. A bushing 127 is inserted into the guide groove 122-3. A through hole is formed in the bushing 127 and a pin 125-a of a link bar 125 to be described later passes through the through hole. The bushing 127 is circular or square in shape so as to be movable along the guide groove 122-3. The guide groove 122-3 is formed in conformity with the layout of the filters F1 to F4. One side of the guide groove 122-3 extends in the first direction and the other side thereof extends in the second direction.

The bushing 127 is made up of a small-diameter bushing 127-a getting into the guide groove 123-3 and a large-diameter bushing 127-b put in contact with a surface of the outer guide plate 122-1 and that of the inner guide plate 122-2. Consequently, as can be seen from FIG. 3, the bushing 127 can move in a plane in contact with the guide plate 122. To prevent the bushing 127 from falling off the guide groove 122-3, a side face of the outer guide plate 122-1 and that of the inner guide plate 122-2 may be formed in such a structure as sandwiches the bushing 127.

The guide plate 122 is fixed to a fixed portion of the X-ray tube unit 10 and is disposed in a fixed positional relation to the X-ray tube 11. That is, the outer guide plate 122-1 is fixed to a housing of the X-ray tube unit 10. Although in FIG. 2 the inner guide plate 122-2 is floating in the air, the inner guide plate 122-2 is connected in at least one position to the outer guide plate 122-1 or to another member. Centrally of the guide plate 122 is formed a first square aperture 122-4 for radiation of an X-ray beam emitted from the X-ray tube 11. Of course, the aperture 122-4 may be a circular aperture.

The drive plate 123 is for moving the bushing 127 along the guide groove 122-3. An outer periphery gear is formed on an outer periphery of the drive plate 123 and it is in mesh with a driving gear 124. The driving gear 124 is connected to the drive motor 21. A link bar 125 capable of rotating 360° is secured to a certain position of the drive plate 123. The link bar 125 has a predetermined length and a pin 125-a is provided at one end of the link bar 125. A front end portion of the pin 125-a is threaded and passes through the through hole of the bushing 127, further through the central hole of the filter plate 121, then comes into engagement with a nut 126. Without specially providing the bushing 127, the thickness of the pin 125-a may be made equal to the width of the guide groove 122-3, thereby allowing the pin 125-a to fulfill the same function as the bushing 127.

The drive plate 123 is fixed to the fixed portion of the X-ray tube unit 10 via a bearing (not shown) and is disposed in a fixed positional relation to the X-ray tube 11. Centrally of the drive plate 123 is formed a second circular aperture 123-1 for radiation of an X-ray beam emitted from the X-ray tube 11. Of course, the aperture 123-1 may be a square aperture. Although reference has been made above to an example in which the outer periphery gear is formed on the outer periphery of the drive plate 123, the outer periphery gear may be substituted by an inner periphery gear formed on an inner periphery of the drive plate 123.

As shown in FIG. 3, the guide plate 122 and the drive plate 123 are disposed in such a manner that the center of the first square aperture 122-4 and that of the second circular aperture 123-1 are coincident with an axis joining the center of the X-ray tube 11 and that of the collimator 13. That is, the X-ray beam emitted from the X-ray tube 11 passes through the filter F in the filter plate 121 and then passes through the first square aperture 122-4. Further, the X-ray beam passes through the second square aperture 123-1, then through the collimator 13 and irradiates a subject (not shown). The filter unit 12 may be reversed right and left in FIG. 3, thereby allowing the X-ray beam to pass through the second circular aperture 123-1, then through the first square aperture 122-4 and thereafter through the filter F in the filer plate 121.

Figure 4A:
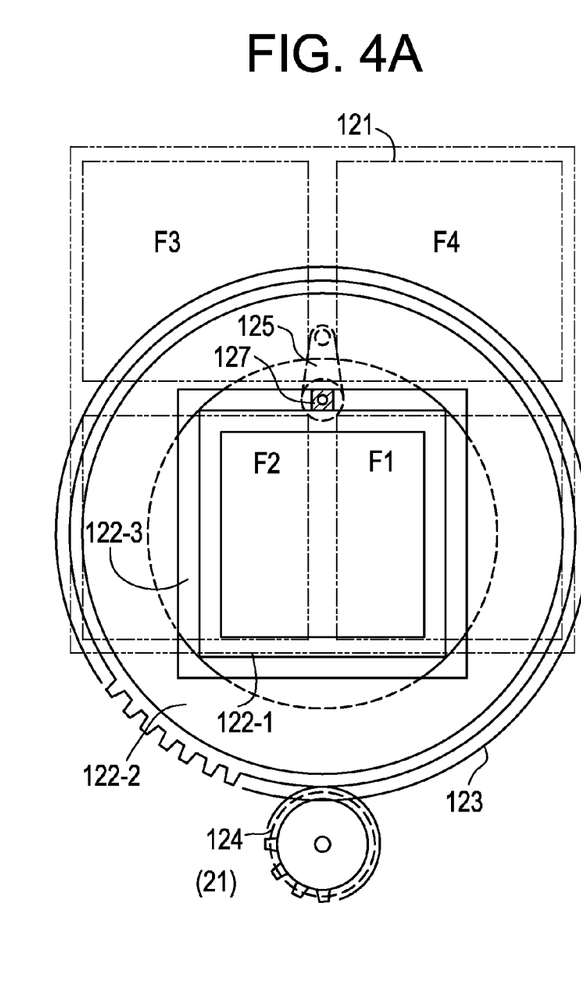
FIG. 4(a) is a plan view of the filter unit 12 and FIG. 4(b) is a drive explaining diagram equivalent to the filter unit 12.

Operation of Filter Unit 12. FIG. 4(a) is a plan view of the filter unit 12 and FIG. 4(b) is a drive explaining diagram equivalent to the filter unit 12.

In FIG. 4(a), upon rotation of the drive motor 21, the drive gear 124 rotates and so does the drive plate 123. With rotation of the drive plate 123, the link bar 125 moves. The pin 125-a of the link bar 125 is connected to the bushing 127 and the bushing 127 moves along the guide groove 122-3, so that the link bar 125 rotates with respect to the drive plate 123.

Since the guide plate 122 is fixed, the filter plate 121 moves along the guide groove 122-3. In the state of FIG. 4(a), an intermediate position between the beam attenuating filters F1 and F2 lies in the central square aperture of the guide plate 122 and the central circular aperture of the drive plate 123. When the drive motor 21 rotates, the filter plate 121 moves along the guide groove 122-3 with respect to the central square aperture of the guide plate 122 and the central circular aperture of the drive plate 123.

Figure 4B:
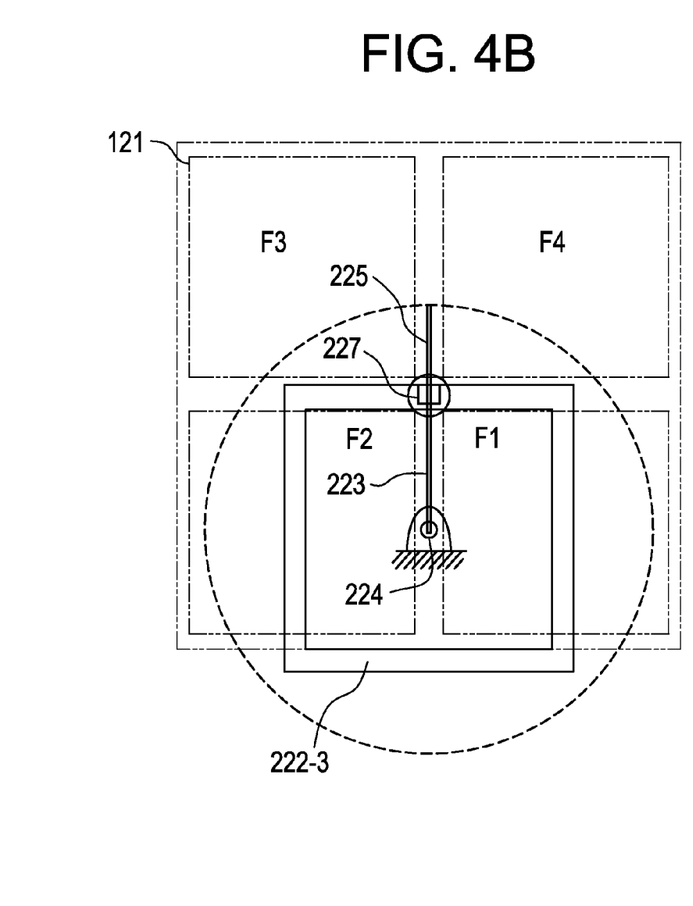

For briefly explaining the operation of the filter plate 121, reference is here made to the drive explaining diagram of FIG. 4(b) equivalent to the plan view of FIG. 4(a).

The guide groove 122-3, the drive plate 123, and the link bar 125, shown in FIG. 4(a), are equivalent to an imaginary guide groove 222-3, an imaginary bar 223, and an imaginary drive member 224, respectively, in FIG. 4(b). Likewise, the link bar 125 and the bushing 127 in FIG. 4(a) are equivalent to an imaginary link bar 225 and an imaginary bushing 227, respectively, in FIG. 4(b).

FIG. 5 comprises operation diagrams showing in what manner the beam attenuation filters are switched one after another from F1 to F4 with use of drive explaining diagrams equivalent to the filter unit 12.

Figure 5A:
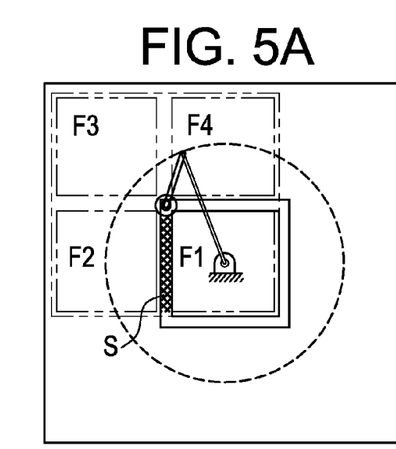
FIGS. 5(a)-5(f) are operation diagrams showing in what manner beam attenuating filters are switched one after another from F1 to F4 with use of drive explaining diagrams equivalent to the filter unit 12.
Figure 5B:
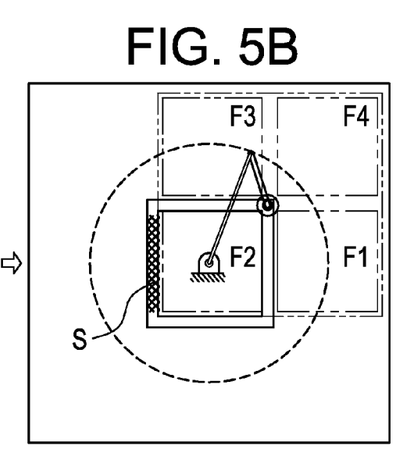
Figure 5C:
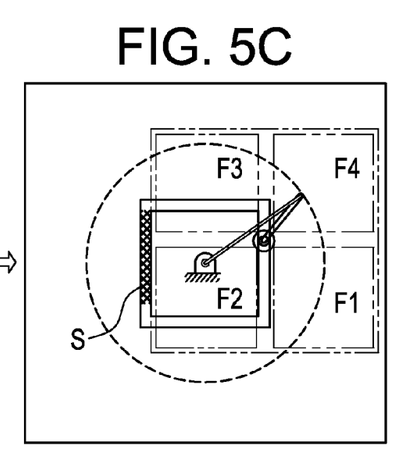

FIG. 5(a) shows a state in which the beam attenuating filter F1 in the filter plate 121 is disposed in both the central square aperture of the guide plate 122 and the central circular aperture of the drive plate 123. With rotation of the drive motor 21, the filter unit 12 moves and, as shown in FIG. 5(b), the beam attenuating filter F2 is disposed in the central square aperture of the guide plate 122. As the drive motor 21 further rotates, the filter unit 12 moves and a shift is made from the beam attenuating filter F2 to the beam attenuating filter F3. FIG. 5(c) shows this shifting state.

Figure 5D:
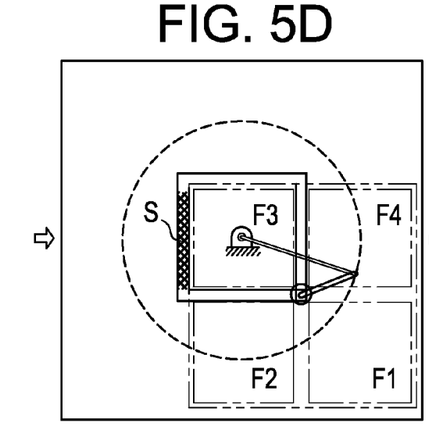
Figure 5E:
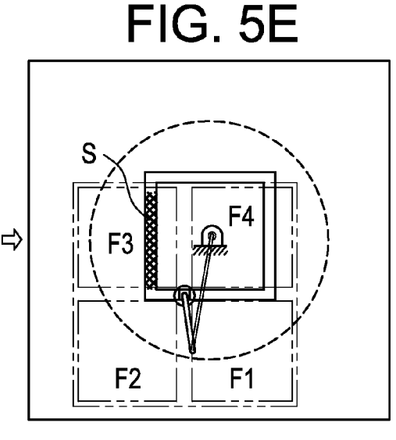

FIG. 5(d) shows a state in which a shift has been made to the beam attenuating filter F3 with movement of the filter unit 12. As the drive motor 21 further rotates, a shift is made from the beam attenuating filter F3 to the beam attenuating filter F4. FIG. 5(e) shows this shifting state. As the filter unit 12 further moves, a shift is made to the state of FIG. 5(f) in which the beam attenuating filter F4 is disposed in the central square aperture of the guide plate 122 and the central circular aperture of the drive plate 123.

Figure 5F:
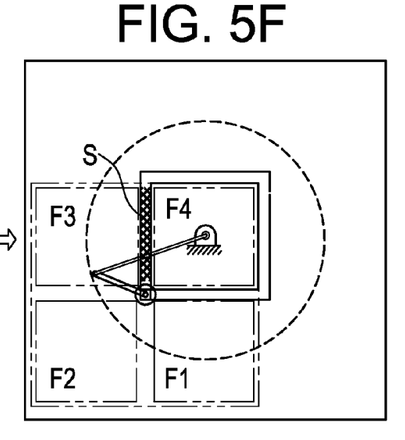

When the drive motor 21 is rotated reverse from its state shown in FIG. 5(f), a shift is made from the beam attenuating filter F4 and through the beam attenuating filters F3 and F2, then the beam attenuating filter F1 returns to the central square aperture of the guide plate 122, as shown in FIG. 5(a). In such an operation of the filter unit 12, the bushing 127 does not pass a hatched portion S of the guide groove 122-3. Therefore, in the hatched portion S it suffices for both outer guide plate 122-1 and inner guide plate 122-2 to be connected with each other.

Figure 6A:
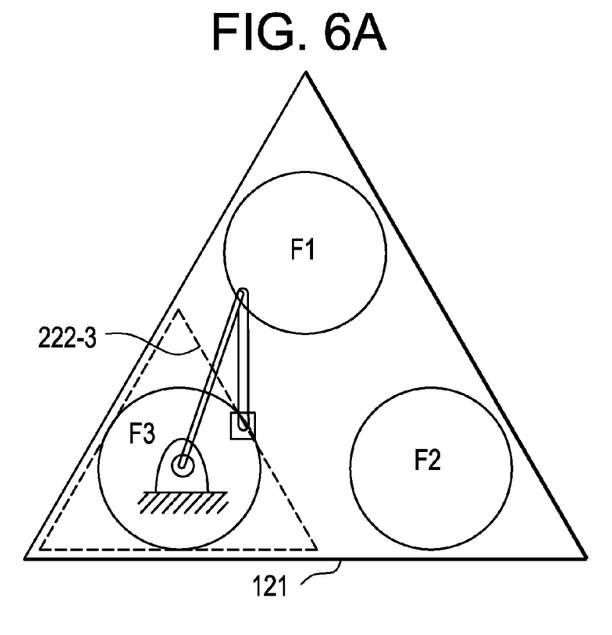
FIG. 6(a) illustrates a filter plate 121 of a regular triangle and FIG. 6(b) illustrates a filter plate 121 of a regular hexagon.
Figure 6B:
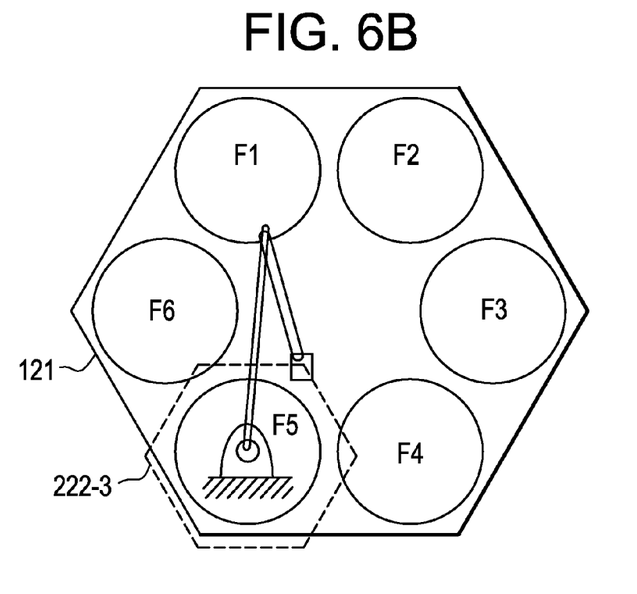

FIG. 6 illustrate filter plates of other shapes with use of explanatory diagrams equivalent to the filter unit 12.

FIG. 6(a) illustrates a filter plate 121 of a regular triangle and FIG. 6(b) illustrates a filter plate 121 of a regular hexagon. The filter plate 121 of a regular triangle has three circular beam attenuating filters F1 to F3. The filter plate 121 of a regular hexagon has six circular beam attenuating filters F1 to F6.

As shown in FIGS. 6(a) and 6(b), there are formed imaginary guide grooves 222-3 of a regular triangle and a regular hexagon, and as imaginary bushings 227 move along the imaginary guide grooves 222-3, the filter plates 121 of a regular triangle and a regular hexagon move and it is possible to replace beam attenuating filters one after another. Thus, as described above in connection with FIGS. 2 to 5, the shape of the filter plate 121 need not be limited to the square shape.

The filter unit 12 may be constructed so as to omit the drive motor 21 and instead permit manual adjustment where required.

Although the construction of the present invention has been described above in terms of an X-ray imaging system for obtaining an X-ray radioscopic image of a subject, the present invention is applicable also to an X-ray tube unit used for example in X-ray tomographic imaging apparatus. Moreover, the present invention is applicable to an industrial X-ray inspection apparatus using X-ray radiation. Further, the present invention is applicable not only to digital X-ray apparatus but also to X-ray apparatus for film.

The invention claimed is:

1. A filter unit comprising:
 a filter plate comprising a first filter, a second filter disposed in a first direction with respect to the first filter, and a third filter disposed in a second direction having a predetermined angle from the first direction;
 a guide plate comprising a guide frame for movement of the filter plate in the first direction and the second direction; and
 a drive device configured to move the filter plate.

2. A filter unit according to claim 1, wherein the drive device comprises a rotary disc and a single drive motor configured to rotate the rotary disc.

3. A filter unit according to claim 2, wherein the guide plate further comprises a first aperture at the center thereof, the rotary disc comprises a second aperture at the center thereof, and the guide plate and the rotary disc are superimposed one on the other.

4. A filter unit according to claim 1, wherein the rotary disc and the filter plate are connected with each other through a link member.

5. A filter unit according to claim 4, wherein a bushing is attached to the link member and is configured to move along the guide frame.

6. A filter unit according to claim 1, wherein the filter plate defines a square outline such that the first direction and the second direction are orthogonal to each other.

7. An X-ray tube unit having an X-ray tube, a collimator and a filter unit, the filter unit comprising:
 a filter plate comprising a first filter, a second filter disposed in a first direction with respect to the first filter, and a third filter disposed in a second direction having a predetermined angle from the first direction;
 a guide plate comprising a guide frame for movement of the filter plate in the first direction and the second direction; and
 a drive device configured to move the filter plate.

8. An X-ray tube unit according to claim 7, wherein the drive device comprises a rotary disc and a single drive motor configured to rotate the rotary disk.

9. An X-ray tube unit according to claim 8, wherein the guide plate further comprises a first aperture at the center thereof, the rotary disc comprises a second aperture at the center thereof, and the guide plate and the rotary disc are superimposed one on the other.

10. An X-ray tube unit according to claim 7, wherein the rotary disc and the filter plate are connected with each other through a link member.

11. An X-ray tube unit according to claim 10, wherein a hushing is attached to the link member and is configured to move along the guide frame.

12. An X-ray tube unit according to claim 7, wherein the filter plate has defines a square outline and the first direction such that the second direction are orthogonal to each other.

13. An X-ray tube unit according to claim 7, wherein the filter plate further comprises a first aperture formed at the center of the guide plate and a second aperture formed at the center of a rotary disc, the first aperture and the second aperture being in alignment with an axis joining the X-ray tube and a collimator aperture.

14. An X-ray imaging system for radiating X-ray to a subject from an X-ray tube unit and picking up a transmitted image, the X-ray tube unit comprising:
 an X-ray tube;
 a collimator; and
 a filter unit comprising:
  a filter plate comprising a first filter, a second filter disposed in a first direction with respect to the first filter, and a third filter disposed in a second direction having a predetermined angle from the first direction;
  a guide plate comprising a guide frame for movement of the filter plate in the first direction and the second direction; and
  a drive device configured to move the filter plate.

15. An X-ray imaging system according to claim 14, wherein the drive device comprises a rotary disc and a single drive motor configured to rotate the rotary disc.

16. An X-ray imaging system according to claim 15, wherein the guide plate further comprises a first aperture at the center thereof, the rotary disc comprises a second aperture at the center thereof, and the guide plate and the rotary disc are superimposed one on the other.

17. An X-ray imaging system according to claim 14, wherein the rotary disc and the filter plate are connected with each other through a link member.

18. An X-ray imaging system according to claim 17, wherein a bushing is attached to the link member and is configured to move along the guide frame.

19. An X-ray imaging system according to claim 14, wherein the filter plate defines a square outline such that the first direction and the second direction are orthogonal to each other.

20. An X-ray imaging system according to claim 14, wherein the filter plate further comprises a first aperture formed at the center of the guide plate and a second aperture formed at the center of a rotary disc, the first aperture and the second aperture being in alignment with an axis joining the X-ray tube and a collimator aperture.

* * * * *